US010208469B2

(12) United States Patent
Becerril Ruiz et al.

(10) Patent No.: US 10,208,469 B2
(45) Date of Patent: Feb. 19, 2019

(54) STERILIZING DEVICE AND METHOD FOR A TOILET (71) Applicant: AERO ENGINEERING, S.L., Barcelona (ES)

(72) Inventors: Jose Luis Becerril Ruiz, Barcelona (ES); David Hernandez Diaz, Barcelona (ES); David Martos Ferreira, Alava (ES)

(73) Assignee: AERO ENGINEERING, S.L., Barcelona (ES)

( * ) Notice: Subject to any disclaimer, the term of this patent is extended or adjusted under 35 U.S.C. 154(b) by 0 days.

(21) Appl. No.: 15/705,481

(22) Filed: Sep. 15, 2017

(65) Prior Publication Data
US 2018/0002910 A1 Jan. 4, 2018

Related U.S. Application Data (63) Continuation of application No. PCT/ES2016/070136, filed on Mar. 2, 2016.

(30) Foreign Application Priority Data

Mar. 18, 2015 (EP) .................................. 15382126

(51) Int. Cl.
*E03D 9/02* (2006.01)
*E03D 9/03* (2006.01)
*E03D 9/00* (2006.01)
*A61L 2/14* (2006.01)
(Continued)

(52) U.S. Cl.
CPC ................ *E03D 9/037* (2013.01); *A61L 2/14* (2013.01); *A61L 2/202* (2013.01); *A61L 2/24* (2013.01);
(Continued)

(58) Field of Classification Search
CPC ........... E03D 9/037; E03D 9/02; E03D 9/007; A61L 2/14; A61L 2/202
(Continued)

(56) References Cited

U.S. PATENT DOCUMENTS 5,680,658 A * 10/1997 Ho ........................... E03D 9/02
261/64.4
7,818,822 B2 10/2010 Martin
(Continued)

FOREIGN PATENT DOCUMENTS

CN 2431330 Y 5/2001
CN 2622267 Y 6/2004
(Continued)

*Primary Examiner* — Huyen Le
(74) *Attorney, Agent, or Firm* — Edell, Shapiro & Finnan, LLC (57) ABSTRACT Sterilizing device for a toilet that includes an ozone generator and an impelling device fluidically connected to the ozone generator that allows discharging the ozone generated into the flush water of the toilet. A controller controls generating the ozone and discharging the ozone into the flush water. A sensor detects the presence or the actuation of a user, the sensor being communicated with the controller. The controller controls the ozone generator depending on a signal received from the sensor. The sterilizing device also includes an ion plasma generator for discharging ion plasma directly into the air adjacent the toilet. The ion plasma generator being controlled by the controller.

19 Claims, 5 Drawing Sheets (51) Int. Cl.
  *A61L 2/20* (2006.01)
  *A61L 2/24* (2006.01)
(52) U.S. Cl.
  CPC ............... *E03D 9/007* (2013.01); *E03D 9/02* (2013.01); *A61L 2202/11* (2013.01); *A61L 2202/14* (2013.01); *A61L 2202/23* (2013.01); *E03D 2009/028* (2013.01)
(58) Field of Classification Search
  USPC .......................................................... 4/227.1
  See application file for complete search history.

(56) References Cited

U.S. PATENT DOCUMENTS

| | | | |
|---|---|---|---|
| 2005/0028254 A1* | 2/2005 | Whiting | A61L 9/015 4/213 |
| 2007/0113327 A1 | 5/2007 | Denkewicz, Jr. et al. | |
| 2010/0064425 A1* | 3/2010 | Ito | E03D 5/105 4/309 |
| 2011/0277227 A1* | 11/2011 | Nonnenmacher | E03D 9/007 4/223 |

FOREIGN PATENT DOCUMENTS

| | | |
|---|---|---|
| CN | 2846551 Y | 12/2006 |
| GB | 2432532 A | 5/2007 |
| JP | 60-31719 A | 2/1985 |
| JP | S6429531 A | 1/1989 |
| JP | H06-33501 A | 2/1994 |
| JP | H10-338958 A | 12/1998 |
| JP | 2004-060419 A | 2/2004 |

* cited by examiner

STERILIZING DEVICE AND METHOD FOR A TOILET

CROSS-REFERENCE TO RELATED APPLICATIONS

This application is a continuation of International Application No. PCT/ES2016/070136, filed Mar. 2, 2016, which relates to and claims the benefit and priority to European Application No. EP15382126.9, filed Mar. 18, 2015. Each of International Application No. PCT/ES2016/070136 and European Application No. EP15382126.9 is hereby incorporated herein by reference in its entirety.

TECHNICAL FIELD

The present invention relates to sterilizing devices for a toilet, and sterilizing methods for a toilet.

BACKGROUND

Toilets are a propitious place for the transmission of organisms such as intestinal bacteria and viruses. Conventional toilets today use water flushing by means of conventional systems for cleaning, this water flushing being controlled manually or automatically by means of a stopcock. Contamination in the bathroom occurs when the toilet water is flushed and organisms are given off from the toilet. The use of bacteriostatic and bactericidal product dispensers for toilets, which inject the product into the flush water by means of a conduit, can reduce the number of organisms given off when flushing the toilet. However, they are rather inefficient because in most cases suitable maintenance is not performed or there is no calibrated relationship between the frequency of use and the amount provided. Furthermore, most of these products are highly toxic chemical products that produce contamination when discharged into water.

Devices that do not use toxic chemical cleaning products are known. In that regard, patent document JPH0633501 A discloses a sterilizing and deodorizing device integrated in a toilet. The device comprises an ozone generator, impelling means consisting of an air pump fluidically connected to the ozone generator that allow discharging the generated ozone into the toilet flush water, and control means that controls generating the ozone and discharging the ozone into the flush water when the user is positioned on the toilet. Part of the ozone discharged into the water of the tank of the toilet is dissolved in the water for subsequently flushing into the toilet bowl, and part of it is discharged from the water tank into the environment of the bathroom in which the toilet is located.

SUMMARY OF THE DISCLOSURE

One aspect of the present disclosure relates to a sterilizing device for a toilet, comprising an ozone generator, impelling means for impelling the generated ozone which is fluidically connected to the ozone generator that allow discharging the ozone generated in the ozone generator into the flush water, control means that controls generating the ozone and discharging the ozone into the flush water, and sensor means for detecting the presence or the actuation of a user, the sensor means being communicated with the control means, and the control means controlling the ozone generator depending on the signal received from the sensor means. The device further comprises an ion plasma generator for discharging ion plasma directly into the air, the control means controlling the ion plasma generator, the control means being configured for not activating the ozone generator and the ion plasma generator simultaneously.

Another aspect of the present disclosure relates to a sterilizing method for a toilet implemented with a sterilizing device for a toilet such as the one defined above.

The sterilizing device comprises an ion plasma generator that generates ions and discharges them into the air of the bathroom in which the toilet is located. It thereby complements the action of the ozone of sterilizing the toilet, prevents odors, and cleans the atmosphere in the bathroom. When ions are generated in water, they alkalinize the water, increasing the pH, which is done to protect coatings. In contrast, when air is ionized, the number of organic volatile elements in the atmosphere around the toilet is reduced, and the sterilizing process is thereby completed.

The efficiency of sterilizing toilets and their environment is thereby increased, it not being necessary to use disinfectants, keeping toilets clean of germs and bacteria, and odors in bathrooms are eliminated. Furthermore, the expense of and contamination caused by chemical cleaning products are reduced.

These and other advantages and features will become evident in view of the drawings and the detailed description.

DETAILED DESCRIPTION

Figure 1:
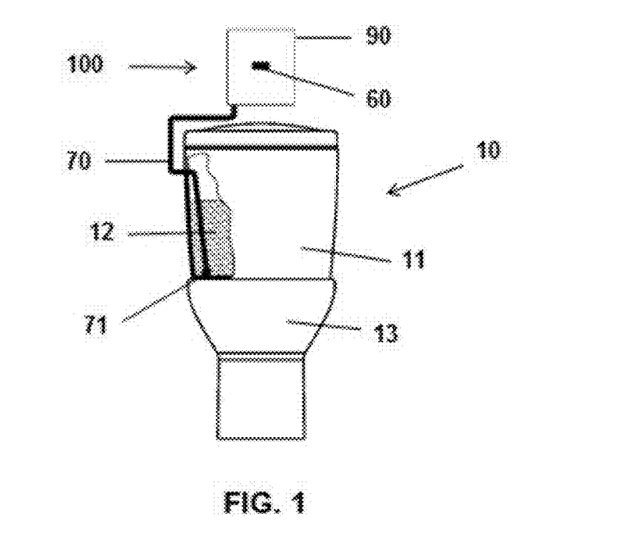
FIG. 1 shows a front view of a toilet with water a sterilizing device according to one embodiment.
Figure 2:
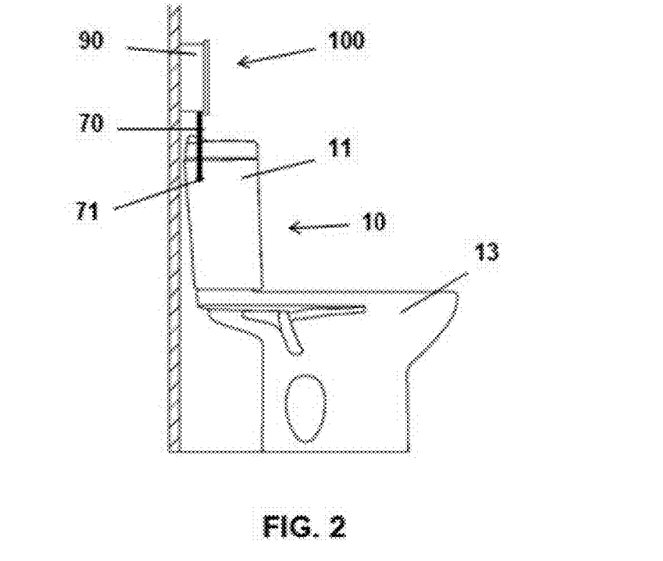
FIG. 2 shows a side view of the toilet of FIG. 1 with the sterilizing device coupled thereto.

FIG. 1 shows a front view of a toilet 10 with a water tank 11 with one embodiment of a sterilizing device 100 coupled to the toilet 10. FIG. 2 shows a side view of the toilet 10 of FIG. 1, with the device 100 coupled thereto.

A toilet water tank of the most important brands available today is capable of storing, for example, according to tank volume, 3 liters of water or less, between 3 and 9 liters of water, or more than 9 liters of water. Complete water flushes thereby correspond to the total stored volume of water, or about half the volume when a half flush is performed.

Figure 3:
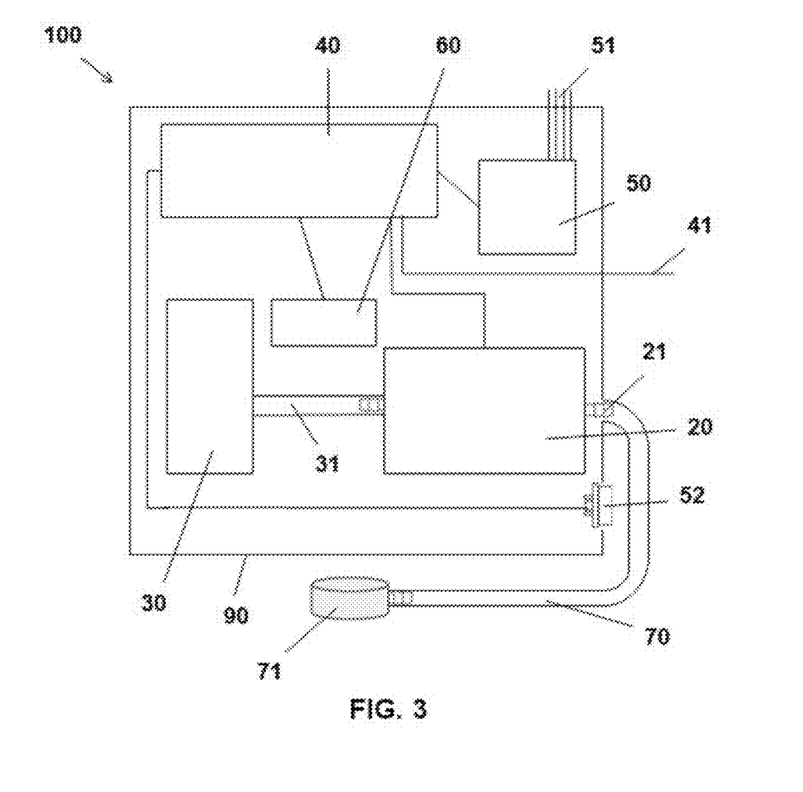
FIG. 3 shows a schematic view of the sterilizing device of FIG. 1, showing its components.

FIG. 3 shows a schematic view of the device 100 of FIG. 1, showing its components. In this embodiment, the device 100 comprises an ozone generator 20 and impelling means 30 fluidically connected to the ozone generator 20 by means of a conduit 31 that allow discharging the ozone generated in the flush water 12 into the toilet 10. The device 100 also comprises control means 40 that controls generating the ozone and discharging the ozone into the flush water 12, and sensor means 60, the sensor means 60 being communicated with the control means 40, and the control means 40 being communicated with the ozone generator 20, the control means 40 controlling the ozone generator 20 depending on the signal received from the sensor means 60.

The ozone generator 20 is a device capable of producing ozone by means of generating a high voltage (corona discharge effect) that produces ozone. Since ozone can neither be stored nor transported, it must be produced in the place where it is going to be used. The use of high frequency and the progress made in electronics have led to being able to use small ozone generators. According to some embodiments, the ozone generator 20 is capable of generating ozone between 200 and 500 mg/hour, obtaining ozone concentrations in flush water 12 of between 1.2 and between 1.6 ppm, i.e., more than enough to sterilize the toilet 10.

In this embodiment, the control means 40 is an electronic card with a microprocessor containing all the data relating to use times and parameters managing ozone release processes and the remaining assigned processes. The control means 40 is connected to the sensor means 60 and to the ozone generator 20. According to one embodiment, the control means 40 is connected to the power grid 41, but it can also use an autonomous energy storage system (not shown in the drawings). The control means 40 also manages indicators (not shown in the drawings) indicating the operation of the device 100.

In this embodiment, the impelling means 30 consists of an air pump that has an air inlet (not shown in the drawings) and is connected to the ozone generator 20 by means of a conduit 31. The impelling means 30 comprise sound and vibration insulation means.

In this embodiment, the sensor means 60 comprises a presence sensor which detects the presence of the user of the toilet 10 at a distance of 65 centimeters, for example. If the user interrupts the sensor means 60, it is understood that the user is using the toilet 60, and after a time n that has been pre-established in the control means 40 has lapsed, for example 3 seconds, the sensor means 60 send a presence signal to the control means 40, and the control means 40 activate the ozone generator 20.

The device 100 further comprises an ion plasma generator 50 for discharging ion plasma directly into the air of the area corresponding to the bathroom where the toilet 10 is located. This ion plasma generator 50 is connected to the control means 40, the control means 40 controlling the ion plasma generator 50. The ion plasma generator 50 can be a negative, positive or bipolar ion generator. According to one embodiment it is a negative ion generator, the negative ions being supplied to the molecules which are contaminated with dust, allergens, etc., which have lost electrons, and which are positively charged. They thereby recover neutrality, which avoids attracting contaminants, even decomposing them in some cases, oxidizing them in other cases, or due to adherence of negative ions, they simply acquire weight and precipitate to the ground, not being included in breathable air. The ion plasma generator 50 of the present embodiment is capable of generating between $10^4$ and $10^6$ electrons/cm$^3$, which is more than enough to complement the sterilizing process of the ozonation process, and eliminating odors in the bathroom space where the toilet 10 is located. In this embodiment of the device 100, the device 100 comprises a switch 52 that allows eliminating activation of the ion plasma generator 50 when the user so desires, the switch 52 sending a signal to the control means 40 with which it is communicated.

According to some embodiments the ozone generator 20, impelling means 30, control means 40, sensor means 60, and ion plasma generator 50 are integrated in a box 90 coupled to the toilet 10. This integration of the different components of the device 100 in a single box 90 provides the device 100 with a portability feature that allows adapting the device 100 to any toilet 10. Furthermore, the box 90 of the device 100 is arranged close to the toilet 100, such that as the ozone generator 20 and ion plasma generator 50 are arranged close to one another, improving sterilizing process efficiency is allowed because the ozonation process of the flush water 12 and the subsequent discharging thereof and sterilization of the toilet bowl 13, are combined with the ionization process of the air of the environment surrounding the toilet 10, ion plasma coming out of the box 90 and entering the air in the room through an outlet 51.

Since the box 90 is arranged outside the toilet 10 but close to same, it is somewhat distanced from the relative humidity of the water tank 11 of the toilet 10, which prevents electrically charging the flush water 12 because the ozone is created by means of high voltage microdischarges. Since the box 90 is on the outside the toilet 10, when the control means 40 activates the ozone generator 20 it starts up the impelling means 30 at the same time, which absorb air from the outside and impel it through the ozone generator 20. The air with ozone is discharged into the flush water 12 of the tank 11 of the toilet 10, coming out of the box 90 through an outlet 21, and circulating through a conduit 70 connecting the outlet 21 of the ozone generator 20 with the flush water 12 of the tank 11. To improve the efficiency of discharging ozone into the water, the conduit 70 comprises a diffuser 71 at one end introduced in the flush water 12, the diffuser 71 being a porous stone according to one embodiment.

Figure 4:
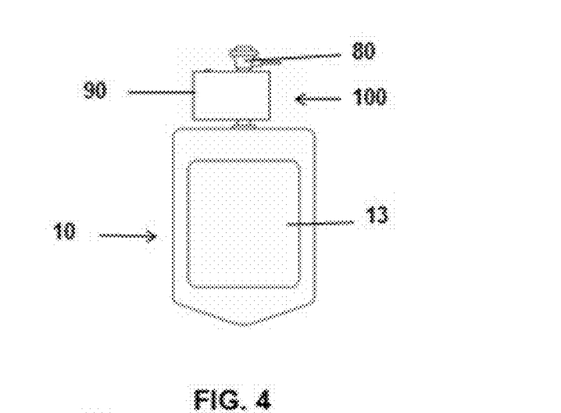
FIG. 4 shows a front view of a urinal-type toilet without a water tank and with a sterilizing device.
Figure 5:
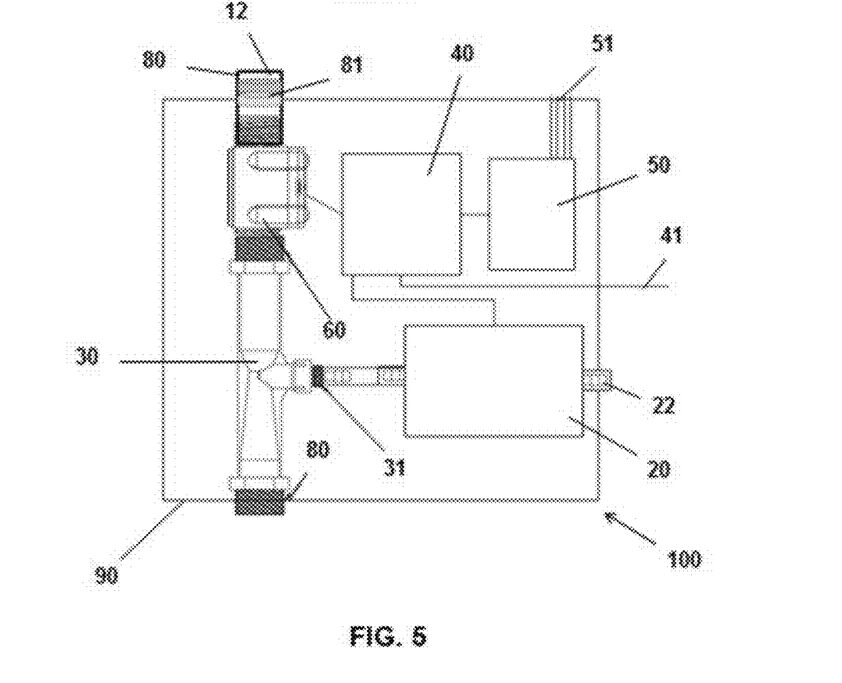
FIG. 5 shows a schematic view of the sterilizing device of FIG. 4, showing its components.

FIG. 4 shows a front view of a urinal-type toilet 10 without a water tank and with a sterilizing device 100 coupled to the toilet 10. FIG. 5 shows a schematic view of the sterilizing device 100 of FIG. 4, showing its components.

Like in the embodiment disclosed above, the sterilizing device 100 comprises an ozone generator 20 and impelling means 30 fluidically connected to the ozone generator 20 by means of a conduit 31 that allow discharging the ozone generated in the flush water 12 into the toilet 10. The device 100 also comprises control means 40 that controls generating the ozone and discharging the ozone into the flush water 12, and sensor means 60 which is communicated with the control means 40, and the control means 40 is in turn communicated with the ozone generator 20, the control means 40 controlling the ozone generator 20 depending on the signal received from the sensor means 60. The sterilizing device 100 also comprises an ion plasma generator 50 for discharging ion plasma directly into the air, the control means 40 controlling the ion plasma generator 50.

According to some implementations the ozone generator 20, ion plasma generator 50 and control means 40 have the same features as in the sterilizing device 100 of FIG. 3.

In this embodiment, the impelling means 30 consists of a three-way Venturi valve. The flush water 12 discharged into the urinal-type toilet 10 flows through an inlet pipe 80. The ozone generator 20, ion plasma generator 50, control means 40, sensor means 60 and impelling means 30 are also integrated in this embodiment in a box 90. This provides the device 100 with a portability feature. This allows installing the device 100 in any urinal-type toilet 10 by coupling the device 100 to the pipe 80 before the inlet into the toilet 10. The impelling means 30 is connected in series with the pipe 80, and is also connected to the ozone generator 20 through the conduit 31.

In this embodiment of the device 100, the sensor means 60 consists of a water flow sensor which is fluidically connected to the pipe 80 upstream of the impelling means 30. The sensor means 60 detect water flow upon passing through the pipe 80. A water filter 81 is fluidically connected to the pipe 80 upstream of the sensor means 60. In this embodiment of the device 100, this water filter 81 comprises two consecutively arranged filters of different mesh, such that the water is filtered before it reaches the ozone injection point.

The water filter 81 has a dual function: on one hand, it cleans the water of impurities, such as lime residues and suspended residues of other materials which could prevent proper injection of ozone or could react with the ozone, generating unwanted byproducts. The filter also causes a drop in water pressure, reducing water flow, which results in water savings of up to 30%.

A urinal-type toilet 10 comprises a shut-off valve (not shown in the drawings) activating the passage of flush water 12 in the pipe 80, this shut-off valve being able to be activated manually by the user or by a signal coming from a presence sensor (not shown in the drawings). In the first case, flush water 12 flows through sensor means 60 that, upon detecting water flow, sends a signal to the control means 40, and the control means 40 activates the ozone generator 20. In the second case, after a time n of presence of the user in front of the toilet 10, the presence sensor sends a signal to the control means 40 which activates the shut-off valve, this shut-off valve allowing water flow through the pipe 80 and through the sensor means 60. The sensor means 60 sends a signal to the control means 40, and the control means 40 activates the ozone generator 20, which takes in air from the outside through an inlet 22 of the box 90. In both cases, the passage of water through the impelling means 30 produces negative pressure in the conduit 31, allowing the passage of ozone generated in the ozone generator 20 into the pipe 80, and the ozone being dissolved in the water flowing through the pipe 80.

In any of the aforementioned two embodiments of the sterilizing device 100 for a toilet 10, the control means 40 is configured to not simultaneously activate the ozone generator 20 and ion plasma generator 50, the ion plasma generator 50 being activated at time intervals during which the ozone generator 20 is not activated.

A sterilizing method for a toilet 10 is implemented for example with a sterilizing device 100 for a toilet 10, as shown in FIGS. 1-5. According to some embodiments the ozone and ions are not released simultaneously, which prevents electric charges during use and improves energy efficiency because the two elements will not be working simultaneously and consuming energy, because when ozone is released into the water with the posterior discharge thereof, ionization is not necessary because ozone takes also the place of ion functionality. The sterilizing method combines ozone-generating cycles and ion plasma-generating cycles, preventing both cycles from overlapping, giving priority to ozone-generating steps. Ionization therefore becomes the perfect complement to the ozone when the ozone is not working, i.e., when the flush water 12 is not used. When the flush water 12 is used, it will be the ozone that acts.

Figure 6:
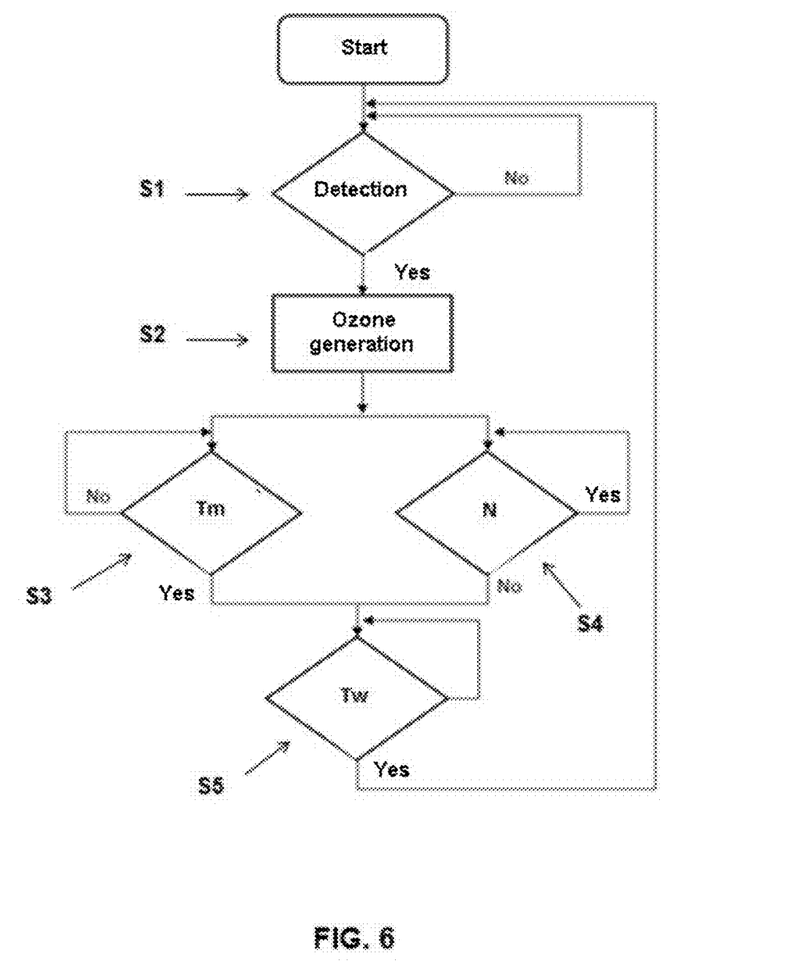
FIG. 6 shows the steps of one embodiment of a sterilizing method corresponding to an ozone-generating cycle.

FIG. 6 shows the steps of a sterilizing method corresponding to an ozone-generating cycle. This cycle allows assuring the amount and conditions of the ozone dissolved in water without reaching excesses causing surplus amounts of ozone being released, and thereby preventing loading the surrounding atmosphere with ozone. The amount of ozone depends on the number of liters of flush water 12 in the water tank 11, or on the water flowing through the pipe 80 in a urinal-type toilet 10. Amounts of ozone released into both the water and the air in any case is thereby controlled, which allows establishing and changing waiting times in order to comply with the degradation time of the ozone in the air and water and to not overload the atmosphere.

A method corresponding to an ozone-generating cycle comprises:

a step of detection S1, in which when the sensor means 60 detect the presence of a user during a time n, or detect water flow flowing through a pipe 80 of the toilet 10, the sensor means sends a signal to the control means 40, a step of generating ozone S2, in which the control means 40 activates the ozone generator 20 when it receives the signal from the sensor means 60, a step of checking a maximum ozone generating time $T_m$ S3, in which the control means 40 checks if the time $T_m$ necessary for generating ozone in the water has lapsed, $T_m$ being a function of the amount of flush water 12 in the toilet 10, and a step of being idle during a waiting time $T_w$ S5, in which the ozone generator 20 enters idle mode after each ozone-generating cycle. This time $T_w$ prevents excessive loads of ozone in the water and, together with the maximum ozone generating time $T_m$, assures efficacy of the device 100, with minimal energy and therefore ozone consumption, preventing the release of uncontrolled ozone loads into the atmosphere of the bathroom.

In toilets 10 with a water tank 11 and in which the sensor means 60 is a presence detector, after the step of a maximum ozone generating time Tm S3 the method corresponding to an ozone-generating cycle comprises:

a step of checking a release time N S4, in which after ozone generation starts, the control means 40 checks if the sensor means 60 is no longer interrupted during a release time N, in which case ozone generation is no longer activated, the release time N being a function of the amount of flush water 12. Minor user movements are therefore prevented from causing ozone generation to be interrupted.

Figure 7:
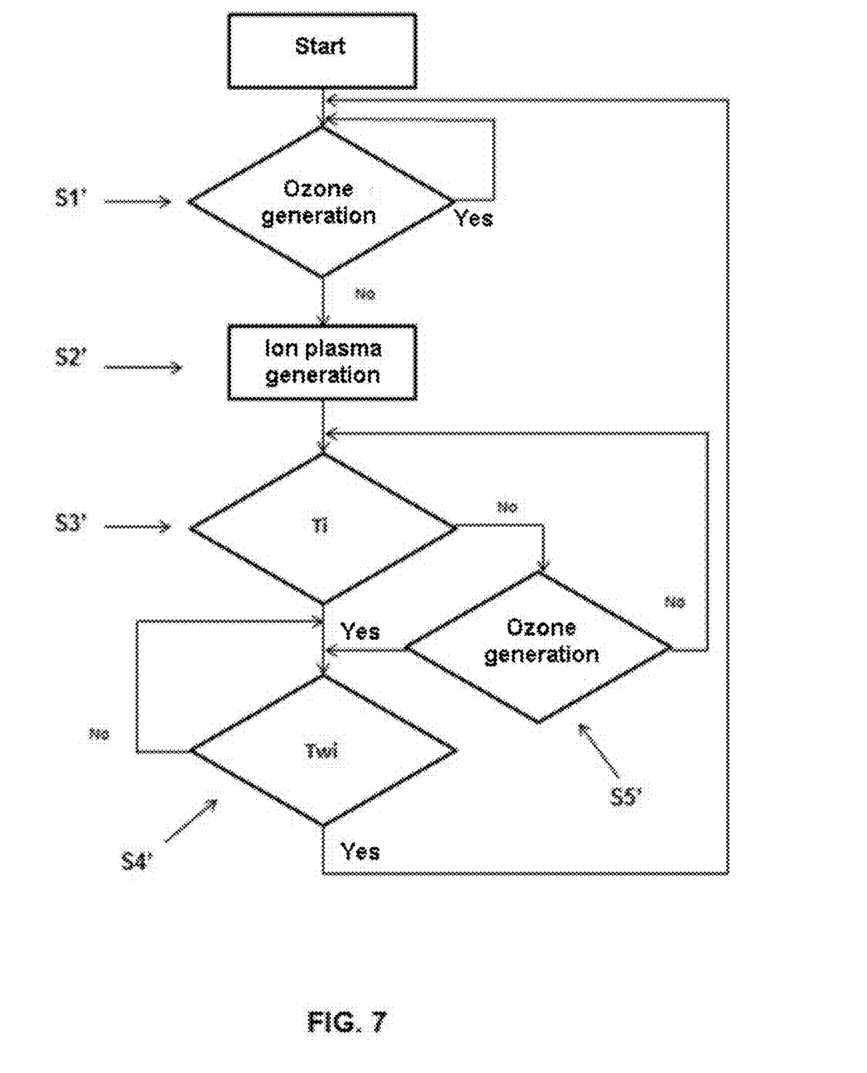
FIG. 7 shows the steps of one embodiment of a sterilizing method corresponding to an ion plasma-generating cycle.

FIG. 7 shows the steps of a sterilizing method corresponding to an ion plasma-generating cycle. The amount of ions depends on the size of the bathroom in which the toilet is located 10. The method thereby prevents overloading the atmosphere with redundant plasma that could create static charges, magnetic fields or even small amounts of ozone.

A method corresponding to an ion plasma-generating cycle comprises:

a step of generating ozone S1', in which the control means 40 activates the ozone generator 20 when it receives the signal from the sensor means 60, a step of generating ion plasma S2', in which the control means 40 activates the ion plasma generator 50 when there is no activated step of generating ozone, and after a predetermined period of time determined by the control means 40, or after a predetermined time of inactivity of the ion plasma generator 50, a step of checking a maximum ion plasma generating time $T_i$ S3', in which the control means 40 checks if the time $T_i$ necessary for generating ion plasma and releasing it into the air has lapsed, $T_i$ being a function of the volume of the size of the bathroom in which the toilet 10 is located, a step of being idle with a waiting time $T_{wi}$ S4', in which the ion plasma generator 50 enters idle mode after each ion plasma-generating cycle. This time $T_{wi}$ prevents excessive loads of ion plasma in the air, and thereby the possibility of generating small magnetic fields or static discharges, minimizing energy consumption, and a step of generating ozone S5', in which the control means 40 activates the ozone generator 20 when it receives the signal from the sensor means 60.

What is claimed is:

1. A sterilizing system for discharging ozone into the flush water of a toilet and for discharging ion plasma into air adjacent the toilet, the sterilizing system comprising:
a sensor,
an ozone generator that produces ozone and is fluidically connected to the flush water,
an ion plasma generator that is configured to produce and release ion plasma into the air,
an impelling device fluidically connected to the ozone generator, the impelling device configured to discharge the ozone produced in the ozone generator into the flush water,
a controller electrically coupled to the sensor and ozone generator, the controller configured to control the activation and deactivation of the ozone generator depending on an output signal of the sensor received by the controller, the controller also being electrically coupled to the ion plasma generator and configured to control the activation and deactivation of the ion plasma generator, the controller configured to activate the ozone generator only when the ion plasma generator is deactivated and to activate the ion plasma generator only when the ozone generator is deactivated.

2. The sterilizing system according to claim 1, wherein the ozone generator is fluidically connected to a flush tank that stores the flush water.

3. The sterilizing system according to claim 2, wherein the impelling device is an air pump.

4. The sterilizing system according to claim 2, further comprising a diffuser located in the flush tank that is fluidically connected to the ozone generator.

5. The sterilizing system according to claim 4, wherein the diffuser is a porous stone.

6. The sterilizing system according to claim 1, wherein the toilet is a urinal-type toilet having a flush water inlet pipe, the ozone generator being fluidically connected to the flush water inlet pipe.

7. The sterilizing system according to claim 6, wherein the impelling device is a venturi valve connected to the flush water inlet pipe.

8. The sterilizing system according to claim 1, wherein the sensor is a presence detector that is configured to emit the output signal upon detecting the presence of a user at the toilet.

9. The sterilizing system according to claim 8, wherein a time of presence n of the user is electronically stored in the controller, the controller configured to activate the ozone generator when the sensor detects the presence of the user and has lapsed the time of presence n.

10. The sterilizing system according to claim 1, wherein the ozone generator, the impelling device and the ion plasma generator are located in a common box that is capable of being coupled to the toilet.

11. The sterilizing system according to claim 10, wherein the controller and/or the sensor are also located in the box.

12. The sterilizing system according to claim 1, wherein the impelling device is a venturi valve and the flush water to the toilet flows through the venturi valve.

13. The sterilizing device according to claim 12, wherein the venturi valve has a flush water inlet and a flush water outlet, the sterilizing system further comprising a water filter located upstream the venturi valve flush water inlet.

14. The sterilizing system according to claim 1, wherein the sensor is a water flow sensor that is configured to emit the output signal upon detecting a flow of the flush water.

15. The sterilizing system according to claim 1, wherein the flush water is delivered to the toilet through a conduit, the sensor being a water flow sensor located in the conduit, the water flow sensor configured to emit the output signal upon detecting a flow of the flush water in the conduit.

16. The sterilizing system according to claim 1, wherein the controller is configured to cause the ion plasma generator to deactivate and the ozone generator to activate upon receiving the output signal of the sensor so that the ion plasma generator and ozone generator are not activated simultaneously.

17. The sterilizing system according to claim 1, wherein the controller stores a maximum ion plasma generating time $T_i$ for maintaining the ion plasma generator activated and a waiting time $T_{wi}$ for maintaining the ion plasma generator deactivated after each step of generating ion plasma, the maximum ion plasma generating time $T_i$ and the waiting time $T_{wi}$ being dependent on a volume of air adjacent the toilet.

18. The sterilizing system according to claim 17, wherein the controller is configured to cause the ion plasma generator to be activated periodically between the waiting times $T_{wi}$ and/or after a predetermined time of ion plasma generator inactivity.

19. The sterilizing system according to claim 1, wherein the controller stores a maximum ozone generating time $T_m$ for maintaining the ozone generator activated and a waiting time $T_w$ for maintaining the ozone generator deactivated after each step of generating ozone being dependent on the amount of flush water delivered to the toilet.

* * * * *